(12) United States Patent
Scherer et al.

(10) Patent No.: US 6,392,057 B1
(45) Date of Patent: May 21, 2002

(54) METHOD FOR THE PRODUCTION OF N,N'-CARBONYLDIAZOLES

(75) Inventors: Johannes Scherer, Leverkusen; Alexander Klausener, Pulheim; Robert Söllner, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/743,880

(22) PCT Filed: Jul. 16, 1999

(86) PCT No.: PCT/EP99/05072

§ 371 Date: Jan. 17, 2001

§ 102(e) Date: Jan. 17, 2001

(87) PCT Pub. No.: WO00/06551

PCT Pub. Date: Feb. 10, 2000

(30) Foreign Application Priority Data

Jul. 28, 1998 (DE) .......................................... 198 33 913

(51) Int. Cl.⁷ ............................................ C07D 403/06
(52) U.S. Cl. ..................................................... 548/313.7
(58) Field of Search ....................................... 548/313.7

(56) References Cited

FOREIGN PATENT DOCUMENTS

| DE | 1033210 | 7/1958 |
| EP | 0 692 476 | 1/1996 |
| WO | 98/31672 | 7/1998 |

OTHER PUBLICATIONS

Org. Synth. Coll. vol. IV, pp. 201–204, (month unavailable) 1968, Coumalic Acid.

Walter W. et al, "Zur Umsetzung Von Azolen Mit Anorganischen Saeurechloriden", Liebigs Annalen der Chemie, No. 11, Jan. 1, 1979, pp. 1756–1767, XP002064142.

Staab H.A. et al, "Notiz Zur Darstellung Von 1.1'–Carbonyl–Di–Imidazol" Chemische Berichte, vol. 96, No. 12, Jan. 1, 1963, XP002033933.

*Primary Examiner*—Floyd D. Higel
*Assistant Examiner*—Golam M. M. Shameem
(74) *Attorney, Agent, or Firm*—Joseph C. Gil; Richard E. L. Henderson

(57) ABSTRACT

The invention relates to a process for the preparation of N,N'-carbonyldiazoles by reacting azoles with phosgene in a solvent, whereby the azole and the phosgene are metered into an aromatic solvent dried by incipient distillation in such a way that in the time in which 1 mol of azole is metered in, from 0.17 to 0.34 mol of phosgene is metered in simultaneously.

12 Claims, No Drawings

METHOD FOR THE PRODUCTION OF N,N'-CARBONYLDIAZOLES

This application is a 317 of PCT/EP99/05072 Jul. 16, 1999.

The present invention relates to an improved process for the preparation of N,N'-carbonyldiazoles by reacting azoles with phosgene.

It has already been disclosed that N,N'-carbonyldiazoles can be obtained if azoles are reacted with phosgene (see DE-B 10 33 210). The solvents proposed here are tetrahydrofuran, other ethers and hydrocarbons, in particular anhydrous tetrahydrofuran and mixtures of tetrahydrofuran with benzene (see Chem. Ber. 96, 3374 (1963) and Org. Synth. Coll. Vol. IV, 201–204 (1968)). The reaction apparently takes place at room temperature, with phosgene being passed into an initially introduced solution of the azoles. This process requires solvents which have been freed from final traces of water. Since this requires the handling of metallic sodium, sodium hydride or calcium hydride, this means the use of extraordinary safety measures for work on an industrial scale. In addition, tetrahydrofuran and other ethers always entail the risk of the formation of explosive peroxides. Furthermore, the process can only be reproduced with difficulty.

These problems are circumvented in a more recent process (EP-A2 692 476) by working at temperatures of from 50 to 120° C. in an aromatic solvent, such as benzene, toluene or chlorobenzene, which has been dried by incipient distillation. In practice, the solvent is firstly dried by incipient distillation, the azole is then introduced and dissolved with warming, and phosgene is then passed in.

However, the procedure of passing phosgene into initially introduced azole solutions is accompanied by the following disadvantages:

If work is carried out at temperatures below 50° C., it is necessary to use solvents such as tetrahydrofuran, which causes problems for the above-mentioned reasons, since both of the azoles and the carbonyldiazoles are insufficiently soluble in the solvents that are simpler to dry and do not tend towards the formation of peroxide, such as benzene, toluene, xylenes or monochlorobenzene, If work is carried out at temperatures above 50° C., the azole hydrochloride precipitate formed in the reaction is obtained as a viscous, tacky mass which adheres strongly to the reactor wall and stirrer and thereby considerably impairs stirrability. The heavy running of the stirrer then limits the maximum possible space yield to relatively low values. On solidification of the precipitate towards the end of the phosgene addition, hard beads then form, which can cause damage to the reaction vessel and its internals (for example stirrer, dip tubes, etc.).

There is therefore still a need for a process for the preparation of N,N'-carbonyldiazoles in which solvents that are difficult to handle and dry and at the same time tacky azole hydrochloride precipitates which cause problems are avoided.

A process has now been found for the preparation of N,N'-carbonyldiazoles of the formula (I)

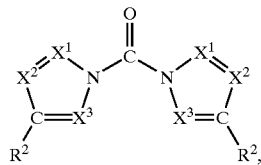

in which $X^1$, $X^2$ and $X^3$, independently of one another, are each $CR^1$ or nitrogen, where $R^1$ is hydrogen or $C_1$–$C_6$-alkyl, and $R^2$ is hydrogen, or $X^1$ and $X^3$ are $CR^1$, where the $R^1$ located on $X^1$ is hydrogen or $C_1$–$C_6$-alkyl, and the $R^1$ located on $X^3$, together with $R^2$, forms a —CH=CH—CH=CH— bridge, and $X^2$ is $CR^1$ or nitrogen, where $R^1$ is hydrogen or $C_1$–$C_6$-alkyl, by reacting azoles of the formula (II)

in which the symbols used are as defined under the formula (I), with phosgene in a solvent, which process is characterized in that the azole of the formula (II) is metered with phosgene into an aromatic solvent which has been dried by incipient distillation, at such a rate that in the time in which 1 mol of azole of the formula (II) is metered in, from 0.17 to 0.34 mol of phosgene is metered in simultaneously.

In the process according to the invention, the azole hydrochloride (for example imidazole hydrochloride) precipitated in the reaction is, surprisingly, always formed and remains as a disperse, crystalline precipitate which does not form any deposits or adhesion to the stirrer or vessel wall. Due to the disperse habit of the precipitate, the stirring resistance is significantly lower than in the procedure which is not according to the invention. Significantly higher reactant concentrations than before can therefore be used in accordance with the invention, which results in a significantly improved space yield compared with the prior art. In accordance with EP-A 2 692 476, a reactant concentration of 12% by weight is used and a space yield of about 70 g/l is achieved, whereas in the process according to the invention, reactant concentrations of, for example, from 28 to 33% by weight are used and space yields of, for example, from 120 to 175 g/l can be achieved. Damage to the reactor and its internals due to hard azole hydrochloride conglomerates can also be excluded.

In the process according to the invention, the azole hydrochloride is in the form of a crystalline precipitate even towards the end of the metering of azoles of the formula (II) and phosgene. It can be washed easily and completely out of the reactor into a filtration device together with the reaction mixture. The filtration times are short owing to the crystallinity of the precipitate.

Preferably, only one azole of the formula (II) is employed in the process according to the invention, and thus a N,N'-carbonyldiazole of the formula (I) in which the two azole rings are identical is obtained.

It is furthermore preferred for one or two of the $X^1$, $X^2$ and $X^3$ moieties in the formulae (I) and (II) to be nitrogen. It is also preferred for $X^1$ to be CH, $X^2$ to be nitrogen and $X^3$ to be $CR^1$, where $R^1$ and $R^2$ together form a —CH=CH—CH=CH— bridge.

Particular preference is given in the process according to the invention to imidazole, benzimidazole, pyrazole or 1,2,4-triazole as the azole of the formula (II). Very particular preference is given to imidazole here.

Phosgene can be employed in the usual technical-grade quality. It is advantageous to employ from 0.2 to 0.3 mol, in particular from 0.22 to 0.27 mol, of phosgene per mole of the azole of the formula (II). It is particularly preferred to employ 0.25 mol of phosgene per mole of the azole of the formula (II).

It is an essential feature of the present invention that the azole of the formula (II) and phosgene are fed to the reaction mixture in a type of simultaneous metering.

Examples of suitable aromatic solvents are benzene, toluene, xylenes, monochlorobenzene, dichlorobenzenes, trichlorobenzenes and mixtures of these solvents. They are dried in a simple manner by incipient distillation before the reaction of the azoles of the formula (II) with phosgene.

The incipient distillation for drying of the solvents can be carried out, for example, by heating the respective solvent, before use, at the boiling point at atmospheric or reduced pressure until discharge of water is no longer observed. In general, from 0.1 to 5% by weight, preferably from 0.5 to 2% by weight, of the solvent are distilled off in this operation.

The azole used can be metered in in the form of a solution or suspension having a temperature of, for example, from 20 to 120° C., preferably from 60 to 100° C., in the above-mentioned solvents or as a melt. Monitoring of the metering rate is simplified by this type of metering.

The process according to the invention can be carried out, for example, at temperatures of from 50 to 120° C., preferably at from 70 to 100° C.

It is advantageous to initially introduce up to 10% by weight, preferably from 0.1 to 1% by weight, of the total amount of the azole into the reaction vessel before commencing the simultaneous metering of the azole and the phosgene, and then to commence the simultaneous metering of azole and phosgene. Thus, the unfavourable situation of phosgene being present in a significant excess (molar ratio phosgene:azole=0.3 or greater) cannot occur, even at the beginning of the reaction. This is because such high molar ratios favour decomposition of the azole with darkening of the reaction mixture.

It is generally advantageous to stir the reaction mixture for some time, for example for from 30 minutes to 5 hours, at elevated temperature after the simultaneous metering-in of the reactants.

The reaction mixture can be worked up, for example, by separating off the resultant azole hydrochloride precipitate by filtration at from 50 to 120° C., preferably at from 70 to 100° C. The filtration succeeds well owing to the consistency of the precipitate.

It has furthermore been found that the N,N'-carbonyldiazole can be isolated from the mother liquor obtained on removal of hydrochloride if the mother liquor is cooled to from +40 to −70° C., preferably from +25 to −20° C., and the product which crystallizes out during this operation is filtered off. The product is obtained in this way in well-crystallized form in purities of greater than 95%.

In accordance with the prior art, by contrast, the mother liquor from the removal of the hydrochloride is evaporated to dryness. Any impurities present in the mother liquor then remain in the product. In addition, the N,N'-carbonyldiazole obtained in accordance with the prior art is partially amorphous, tends to dust and is sensitive to moisture.

Half of the azole employed is formed as azole hydrochloride, which, in accordance with the prior art, obviously has to be disposed of or used elsewhere. It has also been found that it is possible to carry out the process according to the invention using an azole, all or some of which has been obtained from azole hydrochloride, in particular from azole hydrochloride obtained in the synthesis of N,N'-carbonyldiazole as by-product.

The recovery of azoles from azole hydrochlorides can be carried out, for example, by reacting azole hydrochlorides, in particular azole hydrochlorides formed in the synthesis of N,N'-carbonyldiazoles, with a compound of the formula $$M(OR^4)_n \quad (IV),$$

in which n corresponds to the valency of M,

M is an alkali metal or alkaline earth metal, and $R^4$ is as defined under the formula (III), in a solvent mixture comprising firstly an aromatic solvent, such as benzene, toluene, a xylene, monochlorobenzene, a dichlorobenzene, a trichlorobenzene or mixtures thereof, preferably in the solvent in which the synthesis of N,N'-carbonyldiazole was carried out, and secondly a solvent of the formula $$R^4OH \quad (III),$$

in which $R^4$ is hydrogen or $C_1$–$C_4$-alkyl.

$R^4$ in the formulae (III) and (IV) is preferably hydrogen or methyl, and M in the formula (IV) is preferably lithium, sodium or potassium.

After the reaction of the azole hydrochloride with the compound of the formula (IV), it is advantageous to distil off all of the compound of the formula (III), including the compound of the formula (III) formed in the reaction of azole hydrochloride and the compound of the formula (IV), to filter off the resultant salt $MCl_n$ at atmospheric or elevated temperature, and to re-employ the isolated azole for the N,N'-carbonyldiazole synthesis according to the invention, either directly in the aromatic solvent or after removal of the aromatic solvent.

This procedure succeeds particularly well if the compound (IV) employed is LiOH, 30 NaOH or KOH in a solvent mixture comprising water (that is a compound of the formula (III) in which $R^4$=hydrogen) and chlorobenzene, toluene, xylene or 2-methyltetrahydrofuran, and the water is removed by azeotropic distillation, for example by removing it on a water separator, or alternatively if the compound of the formula (IV) employed is sodium methoxide in a solvent mixture comprising methanol on the one hand and chlorobenzene or xylene on the other hand, and the methanol is separated off by distillation, for example by distilling it off from the mixture via an effective column.

In summary, it is surprising that it is possible through the starting-material metering control according to the invention, to form the by-product (azole hydrochloride) in a non-tacky consistency and thus to improve the stirring properties of the reaction solution, to make higher space yields achievable, to ensure easy removal of the azole hydrochloride from the reaction mixture, to exclude damage due to hardened azole hydrochlorides, and to keep the filtration time short. Further advantages of specific embodiments of the present invention are the provision of a work-up in which the N,N'-carbonyldiazoles are produced in crystalline, readily filterable form and in which the azole hydrochloride formed as by-product can be recovered and re-employed in the synthesis of N,N'-carbonyldiazole. The latter means an approximately doubling in the yield of N,N'-carbonyldiazole, based on the azole employed.

EXAMPLES

Example 1

1000 g of chlorobenzene dried by incipient distillation were introduced into a flask and heated to 75° C. A solution of 408.6 g of imidazole in 410 g of dried chlorobenzene were introduced into a dropping funnel heated to 75° C. The 818.6 g of imidazole solution and 158.2 g of phosgene were then passed in simultaneously at 75° C. over the course of 1.5 hours, the former at a rate of 8.6 g/min and the latter at a rate of 100 g/h. When the addition was complete, the mixture was stirred for a further 1 hour at 80° C. while a vigorous stream of nitrogen was passed through. The imidazole hydrochloride precipitate was filtered off and washed with 200 g of chlorobenzene at 80° C. The combined filtrates were cooled to 20° C. The resultant carbonyldiimidazole precipitate was filtered off, washed with 200 g of dried chlorobenzene and dried at 60° C. and 50 mbar, giving 213.7 g of colourless crystals (97.7% carbonyldiimidazole, 85.8% of theory).

Example 2

500 g of chlorobenzene dried by incipient distillation were introduced into a flask and heated to 80° C. A solution of 500.0 g of imidazole in 500.0 g of dried chlorobenzene were introduced into a dropping funnel heated to 75° C. 100 g of the solution were metered into the initially introduced chlorobenzene, and the remaining 900 g of imidazole solution and 200.0 g of phosgene were then passed in simultaneously at 85° C. over the course of 1.5 hours, the former at a rate of 10 g/min and the latter at a rate of 2.2 g/min. When the addition was complete, the mixture was stirred for a further 1 hour at 80° C. while a vigorous stream of nitrogen was passed through. The imidazole hydrochloride precipitate was filtered off and washed with 200 g of chlorobenzene at 80° C. The combined filtrates were cooled to 20° C. The resultant carbonyldiimidazole precipitate was filtered off, washed with 200 g of dried chlorobenzene and dried at 60° C. and 50 mbar, giving 265.0 g of colourless crystals (98.0% carbonyldiimidazole, 89.0% of theory).

Example 3

369.7 g of imidazole hydrochloride (obtained in Example 1) were introduced into 1200 g of chlorobenzene in a distillation apparatus. 486.0 g of a 30% strength by weight methanolic sodium methoxide solution were added dropwise. When the addition was complete, the methanol was distilled off. The sodium chloride formed was filtered off from the distillation bottom product at 100° C., and the filtrate was cooled to 0° C. The precipitated imidazole was filtered off, giving 177.0 g of imidazole.

Example 4

500.0 g of chlorobenzene dried by incipient distillation were introduced into a flask and heated to 75° C. A solution of 323.0 g of fresh imidazole and the 177.0 g of imidazole (obtained in Example 3) in 500.0 g of dried chlorobenzene were introduced into a dropping funnel heated to 75° C. The 1000 g of imidazole solution and 200.0 g of phosgene were then passed in simultaneously over the course of 1.5 hours, the former at a rate of 11 g/min and the latter at a rate of 2.2 g/min. During this operation, the temperature was held at from 76 to 79° C. When the addition was complete, the mixture was stirred for a further 1 hour at 80° C. while a vigorous stream of nitrogen was passed through. The imidazole hydrochloride precipitate was filtered off and washed with 200 g of chlorobenzene at 80° C. The combined filtrates were cooled to 20° C. The resultant carbonyidiimidazole precipitate was filtered off, washed with 200.0 g of dried chlorobenzene and dried at 60° C. and 50 mbar, giving 255.0 g of colourless crystals (97.5% carbonyldiimidazole, 83.3% of theory).

What is claimed is:

1. A process for the preparation of N,N'-carbonyldiazole of formula (I)

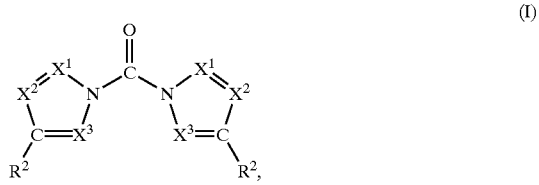

wherein
   (1) $X^1$, $X^2$, and $X^3$, independently of one another, are each $CR^1$ or nitrogen, wherein $R^1$ is hydrogen or $C_1$–$C_6$-alkyl, and
   $R^2$ is hydrogen, or
   (2) $X^1$ and $X^3$ are $CR^1$, wherein the $R^1$ located on $X^1$ is hydrogen or $C_1$–$C_6$-alkyl and the $R^1$ located on $X^3$, together with the $R^2$ on the same ring, forms a —CH=CH—CH=CH— bridge, and
   $X^2$ is $CR^1$ or nitrogen, wherein $R^1$ is hydrogen or $C_1$–$C_6$-alkyl,
comprising reacting an azole of formula (II)

wherein $X^1$, $X^2$, $X^3$, and $R^2$ are as defined for formula (I), with phosgene in an aromatic solvent that has been dried by incipient distillation, wherein the azole of formula (II) is metered with phosgene into the solvent at such a rate that in the time in which each 1 mol of azole of the formula (II) is metered in, from 0.17 to 0.34 mol of phosgene is metered in simultaneously.

2. A process according to claim 1 wherein one or two of the moieties $X^1$, $X^2$, $X^3$ in the formulas (I) and (II) are nitrogen.

3. A process according to claim 1 wherein from 0.2 to 0.3 mol of phosgene are employed per 1 mol of azole of formula (II).

4. A process according to claim 1 wherein the aromatic solvent is benzene, toluene, a xylene, monochlorobenzene, a dichlorobenzene, a trichlorobenzene, or a mixture thereof that has been heated before use at the boiling point at atmospheric or reduced pressure until discharge of water is no longer observed.

5. A process according to claim 1 wherein the reaction is carried out at a temperature in the range from 50 to 120° C.

6. A process according to claim 1 wherein up to 10% by weight of the total mount of the azole is initially introduced into the reaction vessel before commencement of the simultaneous metering of the azole and the phosgene.

7. A process according to claim 1 wherein the reaction mixture is worked up by
   (1) separating off an azole hydrochloride precipitate that forms during the reaction by filtration at from 50 to 120° C., and
   (2) isolating N,N'-carbonyldiazole from the resultant mother liquor from the filtration by cooling the mother liquor to from +40 to −70° C. and filtering off the product that crystallizes.

8. A process according to claim 1 wherein all or some of the azole has been obtained from the corresponding azole hydrochloride.

9. A process according to claim 1 wherein the azole of formula (II) is recovered from the corresponding azole hydrochloride that forms during said process by reacting the azole hydrochloride with a compound of formula (IV)

$$M(OR^4)_n \quad (IV),$$

wherein
n corresponds to the valency of M,
M is an alkali metal or alkaline earth metal, and
$R^4$ is hydrogen or $C_1$–$C_4$-alkyl,
in a solvent mixture comprising an aromatic solvent and a solvent of formula (III)

$$R^4OH \quad (III)$$

wherein $R^4$ is hydrogen or $C_1$–$C_4$-alkyl.

10. A process according to claim 9 wherein the compound of formula (IV) is LiOH, NaOH, or KOH and the solvent mixture comprises a mixture of water with chlorobenzene, toluene, xylene, or 2-methyltetrahydrofuran, and the water is removed by azeotropic distillation.

11. A process according to claim 9 wherein the compound of formula (IV) is sodium methoxide and the solvent mixture comprises a mixture of methanol with chlorobenzene or xylene and the methanol is removed by distillation.

12. A process for the preparation of a N,N'-carbonyldiazole of formula (I)

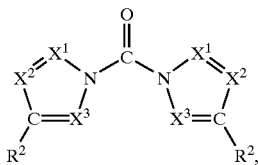
(I)

wherein
(1) $X^1$, $X^2$, and $X^3$, independently of one another, are each $CR^1$ or nitrogen, wherein $R^1$ is hydrogen or $C_1$–$C_6$-alkyl, and
$R^2$ is hydrogen, or
(2) $X^1$ and $X^3$ are $CR^1$, wherein the $R^1$ located on $X^1$ is hydrogen or $C_1$–$C_6$-alkyl and the $R^1$ located on $X^3$, together with the $R^2$ on the same ring, forms a —CH=CH—CH=CH— bridge, and $X^2$ is $CR^1$ or nitrogen, wherein $R^1$ is hydrogen or $C_1$–$C_6$-alkyl, comprising
(a) preparing a dried aromatic solvent by drying an aromatic solvent by heating at the boiling point until discharge of water is not observed,
(b) reacting an azole of formula (II)

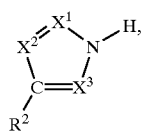
(II)

wherein $X^1$, $X^2$, $X^3$, and $R^2$ are as defined for formula (I), with phosgene in the dried aromatic solvent, wherein the azole of formula (II) is metered with phosgene into the solvent at such a rate that in the time in which each 1 mol of azole of the formula (II) is metered in, from 0.17 to 0.34 mol of phosgene is metered in simultaneously,
(c) separating off a crystalline azole hydrochloride precipitate that forms during the reaction by filtration at from 50 to 120° C.,
(d) isolating crystalline N,N'-carbonyldiazole from the resultant mother liquor by cooling the mother liquor to from +40 to −70° C. and filtering off the crystalline N,N'-carbonyldiazole, and
(e) recovering the azole of formula (II) from the crystalline azole hydrochloride by reacting the crystalline azole hydrochloride with a compound of formula (IV)

$$M(OR^4)_n \quad (IV),$$

wherein
n corresponds to the valency of M,
M is an alkali metal or alkaline earth metal, and
$R^4$ is hydrogen or $C_1$–$C_4$-alkyl,
in a solvent mixture comprising an aromatic solvent and a solvent of formula (III)

$$R^4OH \quad (III)$$

wherein $R^4$ is hydrogen or $C_1$–$C_4$-alkyl.

* * * * *